United States Patent [19]

Kramer et al.

[11] Patent Number: 5,489,447
[45] Date of Patent: Feb. 6, 1996

[54] CARRIER-BOUND KETOCARBOXYLIC ACIDS AS CORROSION INHIBITORS

[75] Inventors: Andreas Kramer, Düdingen, Switzerland; Adalbert Braig, Binzen, Germany

[73] Assignee: Ciba-Geigy Corporation, Tarrytown, N.Y.

[21] Appl. No.: 263,692

[22] Filed: Jun. 20, 1994

[30] Foreign Application Priority Data

Jun. 25, 1993 [CH] Switzerland .................. 1906/93

[51] Int. Cl.$^6$ ........................................ B05D 3/02
[52] U.S. Cl. .......................... 427/388.1; 106/14.13; 106/14.15; 106/14.41; 106/14.42; 106/14.44; 252/388; 252/394; 252/396; 427/388.4; 427/388.5; 562/465; 562/471; 562/496
[58] Field of Search .................... 106/14.13, 14.15, 106/14.41, 14.42, 14.44; 252/388, 394, 396; 562/465, 471, 496; 427/388.1, 388.4, 388.5

[56] References Cited

U.S. PATENT DOCUMENTS 4,909,987  3/1990  Penninger et al. .................. 422/17

FOREIGN PATENT DOCUMENTS

| 0066880 | 12/1982 | European Pat. Off. . |
| 0144663 | 6/1985 | European Pat. Off. . |
| 0412933 | 2/1991 | European Pat. Off. . |
| 0496555 | 7/1992 | European Pat. Off. . |
| 3122907 | 1/1983 | Germany . |

OTHER PUBLICATIONS

Ullman's Encyclopedia of Industrial Chemistry 5th ed., vol. A18 pp. 455–465, no date.
Houben–Weyl Methoden der Organischen Chemie, Bond E5, pp. 398–399 (1985) (no month).
Houben–Weyl, Methoden der Organischen Chemie Band VIII pp. 381–382 (1985) (no month).
Australian Patent Abstract AU-A-84 447/82, Dec. 16, 1982.

*Primary Examiner*—Anthony Green
*Attorney, Agent, or Firm*—Michele A. Kovaleski

[57] ABSTRACT

A description is given of carrier-bound compounds of the formula I

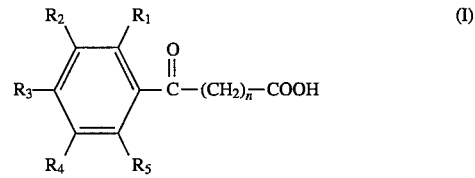

in which $R_1$, $R_2$, $R_3$, $R_4$ and $R_5$ independently of one another are hydrogen, halogen, nitro, cyano, $CF_3$, $C_1$–$C_{15}$alkyl, $C_5$–$C_{12}$cycloalkyl, $C_2$–$C_{15}$alkenyl, $C_1$–$C_{12}$ haloalkyl, $C_1$–$C_{12}$alkoxy, $C_1$–$C_{12}$alkylthio, $C_6$–$C_{10}$aryl, $C_6$–$C_{10}$aryloxy, $C_7$–$C_{12}$arylalkyl, —$CO_2R_6$, —$COR_6$ or

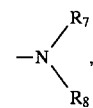

in which at least one of the radicals $R_1$ to $R_5$ is hydrogen, halogen or $C_1$–$C_{15}$alkyl, and, in addition, the radicals $R_1$ and $R_2$, $R_2$ and $R_3$, $R_3$ and $R_4$ or $R_4$ and $R_5$ together with the carbon atoms to which they are attached form a benzo or cyclohexenyl ring, $R_6$ is $C_1$–$C_{20}$alkyl, $C_2$–$C_{20}$alkyl which is interrupted by oxygen, sulfur or >N—$R_9$; or is $C_7$–$C_{12}$arylalkyl, $R_7$ and $R_8$ independently of one another are hydrogen, $C_1$–$C_{24}$alkyl or $C_2$–$C_{24}$alkyl which is interrupted by oxygen, sulfur or >N—$R_9$, $R_9$ is hydrogen or $C_1$–$C_8$alkyl, and n is an integer from the range from 1 to 10, as corrosion inhibitors in coating compositions for protecting metallic surfaces.

18 Claims, No Drawings

CARRIER-BOUND KETOCARBOXYLIC ACIDS AS CORROSION INHIBITORS

The present invention relates to carrier-bound ketocarboxylic acids, to coating compositions comprising an organic film-forming binder, preferably a coating material and the new corrosion inhibitors, and the use thereof in coating compositions for protecting metallic surfaces.

The use of alkali metal, ammonium and amine salts of ketocarboxylic acids as corrosion inhibitors in aqueous systems is known and is described in, for example, U.S. Pat. No. 4,909,987, EP-A-412 933 or EP-A-496 555. The free ketocarboxylic acids are of little suitability for this purpose since, during their incorporation into, for example, aqueous coating systems, compatibility problems are experienced, in particular the coagulation of the coating systems.

DE-A-3 122 907 discloses that the action of readily water-soluble corrosion inhibitors can be improved if they are reversibly bound beforehand to a pulverulent carrier material.

It has now been found that carrier-bound ketocarboxylic acids can be incorporated well into coating systems and that, at the same time, the unwanted coagulation of the coating system is avoided. The carrier-bound ketocarboxylic acids are therefore particularly suitable as corrosion inhibitors in coating compositions for protecting metallic surfaces. The carrier-bound ketocarboxylic acids undergo no interaction with the coating system and are notable in coating compositions for excellent storage stability.

The present invention therefore relates to carrier-bound compounds of the formula I

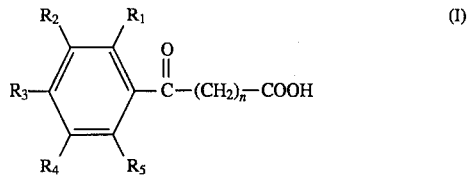

in which $R_1$, $R_2$, $R_3$, $R_4$ and $R_5$ independently of one another are hydrogen, halogen, nitro, cyano, $CF_3$, $C_1$–$C_5$alkyl, $C_5$–$C_{12}$cycloalkyl, $C_2$–$C_{15}$alkenyl, $C_1$–$C_{12}$ haloalkyl, $C_1$–$C_{12}$alkoxy, $C_1$–$C_{12}$alkylthio, $C_6$–$C_{10}$aryl, $C_6$–$C_{10}$aryloxy, $C_7$–$C_{12}$arylalkyl, —$CO_2R_6$, —$COR_6$ or

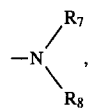

in which at least one of the radicals $R_1$ to $R_5$ is hydrogen, halogen or $C_1$–$C_{15}$alkyl, and, in addition, the radicals $R_1$ and $R_2$, $R_2$ and $R_3$, $R_3$ and $R_4$ or $R_4$ and $R_5$ together with the carbon atoms to which they are attached form a benzo or cyclohexenyl ring, $R_6$ is $C_1$–$C_{20}$alkyl, $C_2$–$C_{20}$alkyl which is interrupted by oxygen, sulfur or >N—$R_9$; or is $C_7$–$C_{12}$arylalkyl, $R_7$ and $R_8$ independently of one another are hydrogen, $C_1$–$C_{24}$alkyl or $C_2$–$C_{24}$alkyl which is interrupted by oxygen, sulfur or >N—$R_9$, $R_9$ is hydrogen or $C_1$–$C_8$alkyl, and n is an integer from the range from 1 to 10.

Halogen is, for example, fluorine, chlorine, bromine or iodine, fluorine, chlorine or bromine is preferred, especially chlorine or bromine.

Alkyl of up to 24 carbon atoms is a branched or unbranched radical such as, for example, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl.

$C_5$–$C_{12}$Cycloalkyl is, for example, cyclopentyl, cyclohexyl, cycloheptyl, cyclooctyl, cyclodecyl or cyclododecyl. Cyclohexyl is preferred.

Alkenyl having from 2 to 15 carbon atoms is a branched or unbranched radical such as, for example, vinyl, 2-propenyl (allyl), 2-butenyl, 3-butenyl, isobutenyl, n-2,4-pentadienyl, 3-methyl-2-butenyl, n-2-octenyl, n-2-dodecenyl or isododecenyl.

Haloalkyl having up to 12 carbon atoms is a branched or unbranched radical such as, for example, chloromethyl, bromoethyl, fluoropropyl, chloropentyl, chlorohexyl, chlorooctyl, chlorodecyl or chlorododecyl.

Alkoxy having up to 12 carbon atoms is a branched or unbranched radical such as, for example, methoxy, ethoxy, propoxy, isopropoxy, n-butoxy, isobutoxy, pentoxy, isopentoxy, hexoxy, heptoxy, octoxy or decoxy.

Alkylthio having up to 12 carbon atoms is a branched or unbranched radical such as, for example, methylthio, ethylthio, propylthio, isopropylthio, n-butylthio, isobutylthio, pentylthio, isopentylthio, hexylthio, heptylthio, octylthio, decylthio or Dodecylthio.

$C_6$–$C_{10}$Aryl is, for example, phenyl or naphthyl.

$C_6$–$C_{12}$Aryloxy is, for example, phenoxy or naphthoxy.

$C_7$–$C_{12}$Arylalkyl is, for example, phenyl-$C_1$–$C_6$alkyl or naphthyl-$C_1$–$C_2$alkyl, for instance benzyl, α-methylbenzyl, α,α-dimethylbenzyl, 2-phenylethyl, 2-naphthylmethyl, 1-naphthylmethyl, 1-naphthylethyl or 2-naphthylethyl.

Alkyl having from 2 up to 24 carbon atoms and interrupted by oxygen, sulfur or >N—$R_9$ is, for example, $CH_3$—O—$CH_2$—, $CH_3$—S—$CH_2$—, $CH_3$—NH—$CH_2$, $CH_3$—N($CH_3$)—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—.

Preferred carrier-bound compounds of the formula I are those in which at least two, in particular 3 of the radicals $R_1$ to $R_5$ are hydrogen.

In formula I n is preferably from 1 to 5, e.g. from 2 to 4, especially 2.

Particularly preferred carrier-bound compounds of the formula I are those in which $R_1$ is hydrogen, $R_2$, $R_3$, $R_4$ and $R_5$ independently of one another are hydrogen, chlorine, bromine, nitro, cyano, $CF_3$, $C_1$–$C_8$alkyl, $C_5$–$C_7$cycloalkyl, $C_2$–$C_8$alkenyl, $C_1$–$C_8$alkoxy, $C_1$–$C_8$alkylthio, phenyl, phenyloxy, benzyl, —$CO_2R_6$, —$COR_6$ or

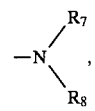

$R_6$ is $C_1$–$C_{12}$alkyl, $C_2$–$C_{12}$alkyl which is interrupted by oxygen; or is benzyl, $R_7$ and $R_8$ independently of one another are hydrogen, $C_1$–$C_8$alkyl or $C_2$–$C_{12}$alkyl which is interrupted by oxygen, and n is an integer from the range from 1 to 5.

Further particularly preferred carrier-bound compounds of the formula I are those in which $R_1$, $R_2$ and $R_4$ are hydrogen, $R_3$ and $R_5$ independently of one another are hydrogen, chlorine, bromine, $CF_3$, $C_1$–$C_8$alkyl, cyclohexyl, $C_1$–$C_8$alkoxy, —$CO_2R_6$, —$COR_6$ or

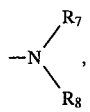

$R_6$ is $C_1$–$C_8$alkyl, $R_7$ and $R_8$ independently of one another are hydrogen or $C_1$–$C_8$alkyl, and n is an integer in the range from 2 to 4.

Particular interest is shown in carrier-bound compounds of the formula I in which $R_1$, $R_2$, $R_4$ and $R_5$ are hydrogen and n is 2.

Special interest is shown in carrier-bound compounds of the formula I in which $R_1$, $R_2$, $R_4$ and $R_5$ are hydrogen, $R_3$ is hydrogen, $C_1$–$C_4$alkyl, $C_1$–$C_4$alkoxy or chlorine, and n is 2.

Very particular preference is given to carrier-bound 3-(4-methylbenzoyl)propionic acid and carrier-bound 3-(4-chlorobenzoyl)propionic acid.

Particularly preferred carrier-bound compounds of the formula I are those in which the carrier is significant in coating technology.

Likewise particularly preferred carrier-bound compounds of the formula I are those in which the carrier is a pigment and/or a filler, as described in Ullmann's Encyclopedia of Industrial Chemistry, Fifth, Completely Revised Edition, Volume A 18, pages 455–465 (1991).

The pigments may be inorganic or organic pigments. Examples of particularly preferred inorganic pigments are iron oxides, titanium oxides and zinc oxides. Examples of particularly preferred organic pigments are urea/formaldehyde adducts and aminoanthraquinones.

Preferred fillers are those based on oxide, hydroxide, silicate and carbonate.

Examples of fillers based on oxide or hydroxide are alumina, magnesium oxide, aluminium hydroxide and magnesium hydroxide.

Examples of fillers based on silicate are ground quartz, kieselguhr, talc, aluminium silicate, magnesium silicate, calcium silicate or zeolite.

Examples of fillers based on carbonate are calcite and chalk.

Very particular preference is given to carrier-bound compounds of the formula I in which the carrier is a filler based on oxide, hydroxide, silicate or carbonate.

Likewise of particular preference are carrier-bound compounds of the formula I in which the carrier is alumina, magnesium oxide, aluminium hydroxide, magnesium hydroxide, kieselguhr, talc, aluminium silicate, calcium carbonate, iron oxide or a urea/formaldehyde adduct.

Special interest is shown in carrier-bound compounds of the formula I in which the carrier is aluminium hydroxide.

Special preference is given to aluminium hydroxide-bound 3-(4-methylbenzoyl)propionic acid and aluminium hydroxide-bound 3-(4-chlorobenzoyl)propionic acid.

The general term "carrier-bound compounds of the formula I" also refers, for example, to "compounds of the formula I absorbed or adsorbed on carriers".

The carrier-bound compounds of the formula I according to the invention can be prepared, for example, as follows: the compounds of the formula I are dissolved in an organic solvent such as, for example, ketones, esters, alcohols or hydrocarbons, with particular examples being acetone, ethyl acetate or ethanol. The carrier is then added with stirring to the clear solution. Subsequently the solvent is removed by distillation, preferably under a slight vacuum and within a temperature range from 20° to 200° C. The dry residue gives a quantitative yield of the carrier-bound compounds of the formula I according to the invention.

The solvent employed is advantageously used in an excess of from 2 to 20 times, preferably from 4 to 15 times and in particular 10 times, by weight relative to the compounds of the formula I employed.

The carrier-bound compounds of the formula I according to the invention contain the compounds of the formula I, for example, in a quantity of from 5 to 70% by weight, preferably from 10 to 50% by weight.

The compounds of the formula I are known and are in some cases commercially available, or can be prepared as described in Houben-Weyl, Methoden der Organischen Chemie [Methods of Organic Chemistry], volume VIII, pp. 381–382 (1952) and volume E5, pp. 398–399 (1985). For example, the Friedel-Crafts acylation of substituted aromatics (benzene and naphthalene derivatives) with cyclic anhydrides gives the compounds of the formula I in excellent yields.

The carrier-bound compounds of the formula I according to the invention are suitable as corrosion inhibitors in coating compositions for protecting metallic surfaces. As such they can be added to all liquid or solid organic materials.

The invention therefore also relates to coating compositions comprising a) an organic film-forming binder and b) as corrosion inhibitor at least one carrier-bound compound of the formula I.

The coating composition is preferably a coating material. Special preference is given to an aqueous coating material.

Examples of coating materials are lacquers, paints or varnishes. These materials always contain an organic film-forming binder, in addition to other, optional components.

Suitable organic film-forming binders in the coating composition are all conventional film-formers for solvent-containing or solvent-free (for example powder coatings or liquid resins) but, in particular, aqueous coating compositions. Examples of such film formers are epoxy resins, polyurethane rosins, amino resins or mixtures thereof; a basic aqueous dispersion or a solution of an acidic resin.

Preferred organic film-forming binders are epoxy resins, polyurethane resins, polyester resins, acrylic resins and copolymer resins thereof, polyvinyl resins, phenolic resins, alkyd resins or mixtures of such resins.

Organic film-forming binders of particular interest are those for aqueous coating compositions, for example alkyd resins; acrylic resins; 2-component epoxy resins; polyurethane resins; polyester resins with conventional saturation; water-dilutable phenolic resins or dispersions derived therefrom; water-dilutable urea resins; or resins based on vinyl/acrylic copolymers.

Considered more specifically, the alkyd resins may be water-dilutable alkyd resin systems which can be employed in air-drying form or in the form of baking systems, optionally in combination with water-dilutable melamine resins; the systems may also, however, be ones which dry oxidatively, by air or with baking, and can optionally be used in combination with aqueous dispersions based on acrylic resins or copolymers thereof, with vinyl acetates, etc.

The acrylic resins may be pure acrylic resins, acrylic ester copolymers, combinations with vinyl resins or copolymers with vinyl monomers such as vinyl acetate or styrene. These systems may be air-drying systems or baking systems.

Water-dilutable epoxy resins, in combination with appropriate polyamine crosslinking agents, exhibit excellent mechanical and chemical resistance. When liquid epoxy resins are used, the addition of organic solvents to aqueous systems can be omitted. The use of solid resins or dispersions of solid resin usually requires the addition of small quantities of solvent in order to improve film formation.

Preferred epoxy resins are those based on aromatic polyols, especially on bisphenols. The epoxy resins are employed in combination with crosslinking agents. The latter may, in particular, be amino- or hydroxy-functional compounds, an acid, an acid anhydride or a Lewis acid. Examples of these are polyamines, polyaminoamides, polysulfide-based polymers, polyphenols, boron fluorides and complex compounds thereof, polycarboxylic acids, 1,2-dicarboxylic anhydrides or pyromellitic dianhydride.

Polyurethane resins are derived from polyethers, polyesters and polybutadienes having terminal hydroxyl groups, on the one hand, and from aliphatic or aromatic polyisocyanates on the other hand.

Examples of suitable polyvinyl resins are polyvinyl butyral, polyvinyl acetate or copolymers thereof.

Suitable phenolic resins are synthetic resins in whose synthesis phenols are the principal component; in other words, in particular, phenol-, cresol-, xylenol- and resorcinol-formaldehyde resins, alkylphenolic resins and condensation products of phenols with acetaldehyde, fufurol, acrolein or other aldehydes. Modified phenolic resins are also of interest.

The coating compositions may additionally contain one or more components from the group consisting of pigments, dyes, fillers, flow control agents, dispersants, thixotropic agents, adhesion promoters, antioxidants, light stabilizers or curing catalysts. They may also contain other known anticorrosive agents, for example anticorrosion pigments such as pigments containing phosphate or borate, or metal oxide pigments, or other organic or inorganic corrosion inhibitors, for example salts of nitroisophthalic acid, phosphoric esters, industrial amines or substituted benzotriazoles.

Examples of additional pigments are titanium dioxide, iron oxide, aluminium bronze or phthalocyanine blue.

Examples of additional fillers are talc, alumina, aluminium silicate, barytes, mica or silica.

Flow control agents and thixotropic agents are based, for instance, on modified bentonites.

Adhesion promoters are based, for example, on modified silanes.

A further advantage is the addition of basic fillers or pigments, which in certain binder systems bring about a synergistic effect in terms of corrosion inhibition. Examples of such basic fillers and pigments are calcium carbonate or magnesium carbonate, zinc oxide, zinc carbonate, zinc phosphate, magnesium oxide, alumina, aluminium phosphate or mixtures thereof. Examples of basic organic pigments are those based on aminoanthraquinone.

The corrosion inhibitors according to the invention can be added to the coating material during its production, for example during the dispersion of the pigment by milling, or the inhibitor is dispersed in a solvent and subsequently stirred into the coating composition.

The carrier-bound compounds of the formula I according to the invention are expediently used in a quantity of from 0.1 to 20% by weight, preferably from 0.5 to 15% by weight, based on the total solids content of the coating composition.

The coating materials can be applied to the substrate by the conventional methods, for example by spraying, dipping, brushing or by electrodeposition. In many cases a plurality of coats are applied. The corrosion inhibitors are primarily added to the primer coat, since they act especially at the metal/coating interface. However, it is also possible for them to be added in addition to the intermediate coat or topcoat. Depending on whether the binder is a physically, chemically or oxidatively drying resin or a heat-curing or radiation-curing resin, the coating is cured at room temperature or by heating (baking) or by irradiation.

The coating material is preferably a primer for metallic substrates such as, for example, iron, steel, copper, zinc or aluminium, and alloys thereof.

In addition to the anticorrosive action, the carrier-bound compounds of the formula I according to the invention have the advantage that they favourably affect the adhesion of coating material to metal and do not impair the storage stability of the coating compositions according to the invention.

A preferred embodiment of the present invention is, therefore, the use of carrier-bound compounds of the formula I as corrosion inhibitors in coating compositions for metallic surfaces.

The present invention also relates to a method of protecting a corrodable metal substrate, which comprises applying to the substrate a coating composition which contains a) an organic film-forming binder and b) as corrosion inhibitor at least one carrier-bound compound of the formula I, and subsequently drying and/or curing this composition.

The examples which follow illustrate the invention in more detail. Data in parts or percentages is by weight.

EXAMPLE 1

Preparation of carrier-bound 3-(4-methylbenzoyl)propionic acid.

56.6 g ®Millicarb [calcium carbonate (Omya)] are added at room temperature to a solution of 10.0 g of 3-(4-methylbenzoyl)propionic acid in 100 ml of acetone. The suspension is stirred at room temperature for about an hour and then concentrated under a slight vacuum at from 50° to 70° C. The residue gives 66.6 g of ®Millicarb-bound 3-(4-methylbenzoyl)propionic acid (compound (101), Table 1). This product contains the 3-(4-methylbenzoyl)propionic acid, with respect to the overall weight, in a proportion of 15% by weight (loading concentration).

In analogy to Example 1, compounds (102) to (112) are prepared from 3-(4-methylbenzoyl)propionic acid with the appropriate amounts of carriers such as ®Bayferrox 130 ME [red iron oxide (Bayer AG)], ®Microtalc AT 1 [Norwegian], ®Aerosil 300 [amorphous silicic acid (Degussa)], ®ASP 170 [aluminium silicate (Engelhard Corp.)], ®BACO LV 9 [aluminium trihydroxide (BA Chemicals Ltd.)], ®BACO SF 7 [aluminium trihydroxide (BA Chemicals Ltd.)], ®Pergopak M3 [urea/formaldehyde condensate (Martinswerke GmbH)] and ®BACO FR F 85 [aluminium trihydroxide (BA Chemicals Ltd.)] (cf. Table 1).

TABLE 1

3-(4-Methylbenzoyl)propionic acid bound on carriers

| Compound | Carrier | Carrier analysis | Average particle size (μM) | Loading concentration (% by weight) |
|---|---|---|---|---|
| 101 | Millicarb | $CaCO_3$ | 3 | 15 |
| 102 | Bayferrox 130 ME | $Fe_2O_3$ | 0.2 | 20 |
| 103 | Microtalc AT 1 | $SiO_2/MgO$ | 0.84 | 16.5 |
| 104 | Aerosil 300 | $SiO_2$ | 0.07 | 50 |
| 105 | ASP 170 | $SiO_2/Al_2O_3$ | 0.55 | 23 |
| 106 | BACO LV 9 | $Al(OH)_3$ | 5 | 16.6 |
| 107 | BACO SF 7 | $Al(OH)_3$ | 1 | 21 |
| 108 | Pergopak M3 | urea/$CH_2O$ | 5 | 50 |
| 109 | BACO FR F 85 | $Al(OH)_3$ | 6 | 20 |
| 110 | BACO FR F 85 | $Al(OH)_3$ | 6 | 30 |
| 111 | BACO FR F 85 | $Al(OH)_3$ | 6 | 40 |
| 112 | BACO FR F 85 | $Al(OH)_3$ | 6 | 50 |

EXAMPLE 2

Preparation of aluminium hydroxide-bound 3-(4-chlorobenzoyl)propionic acid (compound (113)).

7.5 g of ®BACO FR F 85 [aluminium trihydroxide (BA Chemicals Ltd.)] are added at room temperature to a solution of 5.0 g of 3-(4-chlorobenzoyl)propionic acid in 100 ml of ethanol. The suspension is stirred at room temperature for about an hour and then the solvent is distilled off under a slight vacuum. The residue gives 12.5 g of ®BACO FR F 85-bound 3-(4-chlorobenzoyl)propionic acid (compound (113)). The loading concentration is 40% by weight.

EXAMPLE 3

Preparation of aluminium hydroxide-bound 3-(4-methoxybenzoyl)propionic acid (compound (114)).

7.5 g of ®BACO FR F 85 [aluminium trihydroxide (BA Chemicals Ltd.)] are added at room temperature to a solution of 5.0 g of 3-(4-methoxybenzoyl)propionic acid in 100 ml of ethanol. The suspension is stirred at room temperature for about an hour and then the solvent is distilled off under a slight vacuum. The residue gives 12.5 g of ®BACO FR F 85-bound 3-(4-methoxybenzoyl)propionic acid (compound (114)). The loading concentration is 40% by weight.

EXAMPLE 4

Testing of Millicarb-bound 3-(4-methylbenzoyl)propionic acid (compound (101)) in acrylic dispersion based on Maincote HG-54 as corrosion inhibitor.

To prepare the coating composition based on Maincote HG-54, components 1 to 8 (formulation without additives) or components 1 to 9 (formulation with additive) are employed in the order given (cf. Table 2).

TABLE 2

Acrylic dispersion based on Maincote HG-54

| Composition | Example 4a % by weight | Example 4b % by weight |
|---|---|---|
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |
| 6) Acrysol RM 8[e] | 0.60 | 0.60 |
| 7) Bayferrox 130 ME[f] | 5.72 | 5.72 |
| 8) Millicarb[g] | 17.40 | 11.10 |
| 9) Corrosion inhibitor (compound (101)) | — | 6.30 |
| 10) Butyldiglycol | 3.67 | 3.67 |
| 11) Maincote HG-54[h] | 58.70 | 58.70 |
| 12) Texanol[i] | 1.50 | 1.50 |
| 13) Dibutyl phthalate[k] | 1.50 | 1.50 |
| 14) Sodium nitrite (13.8% in water)[l] | 0.80 | 0.80 |
| 15) Drew T 4310[m] | 0.32 | 0.32 |
| 16) Ammonia solution (25%) | 0.30 | 0.30 |
| Total | 100.00 | 100.00 |

Total solids content: 47%; pH: 8 to 8.5; [a] ®Methylcarbitol: diethylene glycol monomethyl ether (Union Carbide); [b] ®Orotan 165: dispersion auxiliary (Rohm & Haas); [c] ®Triton CF 10: nonionic wetting agent (Rohm & Haas); [d] ®Drew Plus TS 4380: antifoam (Drew Chem. Corp.); [e] ®Acrysol RM 8: nonionic thickener (Rohm & Haas); [f] ®Bayferrox 130 ME: red iron oxide (Bayer AG); [g] ®Millicarb: Calcium carbonat (Omya); [h] ®Maincote HG-54: acrylic dispersion, 41.5% in deionized water (Rohm & Haas); [i] ®Texanol: coalescent (Eastman Chem. Prod., Inc.); [k] dibutyl phthalate: plasticizer (Eastman Chem. Prod., Inc.); [l] sodium nitrite: rust-film inhibitor (Fluka); [m] ®Drew T 4310: nonionic antifoam (Drew Chem. Corp.).

Components 1 to 8 and 1 to 9 are dispersed using a high-speed stirrer at 3000 revolutions/minute to a (particle) fineness of <15 μm. The result of dispersion of the pigment paste thus obtained is assessed by determining the grindometer value (ISO 1524). The quantity employed of the corrosion inhibitor according to the invention in the current example, as in the following examples, is calculated such that, independently of the degree of loading of the carrier with 3-(4-methylbenzoyl)propionic acid, the content of active substance is 1% or 2%, respectively, based on the total solids content of the coating formulation (total solids content: 47%).

To complete the preparation of the coating composition components 10 to 16 as in Table 2 are added, in the order given, at a reduced stirring speed (1000 revolutions/minute). Subsequently the pH of the formulation is checked and is adjusted prior to application, if appropriate, with ammonia solution (25%) to a pH of from 8 to 8.5.

The coating composition can be applied in undiluted form by airless spraying or, after dilution, by brushing, rolling or conventional spraying. For application by conventional spraying the formulations are diluted to a spray viscosity of from 22 to 23 seconds (Ford cup 4; DIN 53 211). Diluent: butylglycol/deionized water=1:1 (g/g).

The formulation is applied to steel panels (10 times 15 cm) of type Q-Panel R (cold-rolled, untreated steel; manufacturer: The Q-Panel Company, Cleveland, USA) in a coat thickness which is 50 μm after drying (drying conditions: 10 days at room temperature).

Before the commencement of weathering the "coating films" are subjected to defined damage (70 times 0.5 mm) in the form of a parallel cut (i.e. parallel to the longest panel edge) using a Bonder crosshatch instrument (model 205; manufacturer/marketing: Lau, 5870 Hemer/Germany). The panel edges are protected by applying an edge protector (®Icosit 255; manufacturer: Inertol AG, Winterthur, Switzerland).

The samples are then subjected to rapid weathering in a humidity test (ASTM D 4585-87) for 330 hours or a salt-spray test (DIN 50 021 SS) for 168 hours. The results are compiled in Table 3. The results are evaluated based on the relevant DIN standards according to an evaluation key, by indicating a corrosion protection factor CPF. The CPF is an additive factor based on an assessment of the coating (film) and of the steel and has a maximum value of 12 points. The individual maximum values for the coating (film) and the steel are points. The larger the numbers, the better the protection from corrosion.

TABLE 3

| | Humidity test, 330 hours | | |
|---|---|---|---|
| Coating composition | CPF film | CPF metal | CPF |
| Example 4a | 3.6 | 1.3 | 4.9 |
| Example 4b | 5.4 | 6.0 | 11.4 |

EXAMPLE 5

Testing of Bayferrox 130 ME-bound 3-(4-methylbenzoyl)propionic acid (compound (102)) in acrylic dispersion based on Maincote HG-54 as corrosion inhibitor.

The coating composition based on Maincote HG-54 is prepared in analogy to Example 4, employing components 1 to 16 in the order given (cf. Table 4).

TABLE 4

| Acrylic dispersion based on Maincote HG-54 | | |
|---|---|---|
| Composition | Example 5a % by weight | Example 5b % by weight |
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |
| 6) Acrysol RM 8[e] | 0.60 | 0.60 |
| 7) Bayferrox 130 ME[f] | 5.72 | 0.97 |
| 8) Millicarb[g] | 17.40 | 17.40 |
| 9) Corrosion inhibitor (compound (102)) | — | 4.75 |
| 10) Butyldiglycol | 3.67 | 3.67 |
| 11) Maincote HG-54[h] | 58.70 | 58.70 |
| 12) Texanol[i] | 1.50 | 1.50 |
| 13) Dibutyl phthalate[k] | 1.50 | 1.50 |
| 14) Sodium nitrite (13.8% in water)[l] | 0.80 | 0.80 |
| 15) Drew T 4310[m] | 0.32 | 0.32 |
| 16) Ammonia solution (25%) | 0.30 | 0.30 |
| Total | 100.00 | 100.00 |

For notes a) to m) see Table 2.

The application of the formulation to steel panels of type Q-Panel R, the implementation of the humidity test (330 hours) and the determination of the corrosion protection factors CPF are effected by analogy with the method described in Example 4. The results are compiled in Table 5. The larger the numbers, the better the protection against corrosion.

TABLE 5

| | Humidity test, 330 hours | | |
|---|---|---|---|
| Coating composition | CPF film | CPF metal | CPF |
| Example 5a | 3.6 | 1.3 | 4.9 |
| Example 5b | 5.4 | 6.0 | 11.4 |

EXAMPLE 6

Testing of Microtalc AT 1-bound 3-(4-methylbenzoyl)propionic acid (compound (103)) in acrylic dispersion based on Maincote HG-54, as corrosion inhibitor.

The coating composition based on Maincote HG-54 is prepared in analogy to Example 4 employing components 1 to 17 in the order given (cf. Table 6).

TABLE 6

| Acrylic dispersion based on Maincote HG-54 | | |
|---|---|---|
| Composition | Example 6a % by weight | Example 6b % by weight |
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |
| 6) Acrysol RM 8[e] | 0.60 | 0.60 |
| 7) Bayferrox 130 ME[f] | 5.72 | 5.72 |
| 8) Millicarb[g] | 11.70 | 11.70 |
| 9) Microtalc AT 1 | 5.70 | — |
| 10) Corrosion inhibitor (compound (103)) | — | 5.70 |
| 11) Butyldiglycol | 3.67 | 3.67 |
| 12) Maincote HG-54[h] | 58.70 | 58.70 |
| 13) Texanol[i] | 1.50 | 1.50 |
| 14) Dibutyl phthalate[k] | 1.50 | 1.50 |
| 15) Sodium nitrite (13.8% in water)[l] | 0.80 | 0.80 |
| 16) Drew T 4310[m] | 0.32 | 0.32 |
| 17) Ammonia solution (25%) | 0.30 | 0.30 |
| Total | 100.00 | 100.00 |

For notes a) to m) see Table 2.

The application of the formulation to steel panels of type Q-Panel R, the implementation of the humidity test (330 hours) and the determination of the corrosion protection factors CPF are effected by analogy with the method described in Example 4. The results are compiled in Table 7. The larger the numbers, the better the protection against corrosion.

TABLE 7

| | Humidity test, 330 hours | | |
|---|---|---|---|
| Coating composition | CPF film | CPF metal | CPF |
| Example 6a | 4.0 | 2.0 | 6.0 |
| Example 6b | 6.0 | 6.0 | 12.0 |

EXAMPLE 7

Testing of Aerosil 300-bound 3-(4-methylbenzoyl)propionic acid (compound (104)) in acrylic dispersion based on Maincote HG-54, as corrosion inhibitor.

The coating composition based on Maincote HG-54 is prepared in analogy to Example 4 employing components 1 to 17 in the order given (cf. Table 8).

TABLE 8

Acrylic dispersion based on Maincote HG-54

| Composition | Example 7a % by weight | Example 7b % by weight |
|---|---|---|
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |
| 6) Acrysol RM 8[e] | 0.60 | 0.60 |
| 7) Bayferrox 130 ME[f] | 5.72 | 5.72 |
| 8) Millicarb[g] | 15.50 | 15.50 |
| 9) Aerosil 300 | 1.90 | — |
| 10) Corrosion inhibitor (compound (104)) | — | 1.90 |
| 11) Butyldiglycol | 3.67 | 3.67 |
| 12) Maincote HG-54[h] | 58.70 | 58.70 |
| 13) Texanol[i] | 1.50 | 1.50 |
| 14) Dibutyl phthalate[k] | 1.50 | 1.50 |
| 15) Sodium nitrite (13.8% in water)[l] | 0.80 | 0.80 |
| 16) Drew T 4310[m] | 0.32 | 0.32 |
| 17) Ammonia solution (25%) | 0.30 | 0.30 |
| Total | 100.00 | 100.00 |

For notes a) to m) see Table 2.

The application of the formulation to steel panels of type Q-Panel R, the implementation of the humidity test (330 hours) and the determination of the corrosion protection factors CPF are effected by analogy with the method described in Example 4. The results are compiled in Table 9. The larger the numbers, the better the protection against corrosion.

TABLE 9

| Coating composition | Humidity test, 330 hours | | |
|---|---|---|---|
| | CPF film | CPF metal | CPF |
| Example 7a | 3.8 | 3.6 | 7.4 |
| Example 7b | 5.3 | 6.0 | 11.3 |

EXAMPLE 8

Testing of ASP 170-bound 3-(4-methylbenzoyl)propionic acid (compound (105)) in acrylic dispersion based on Maincote HG-54, as corrosion inhibitor.

The coating composition based on Maincote HG-54 is prepared in analogy to Example 4, employing components 1 to 17 in the order given (cf. Table 10).

TABLE 10

Acrylic dispersion based on Maincote HG-54

| Composition | Example 8a % by weight | Example 8b % by weight |
|---|---|---|
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |
| 6) Acrysol RM 8[e] | 0.60 | 0.60 |
| 7) Bayferrox 130 ME[f] | 5.72 | 5.72 |
| 8) Millicarb[g] | 13.25 | 13.25 |
| 9) ASP 170 | 4.15 | — |
| 10) Corrosion inhibitor (compound (105)) | — | 4.15 |
| 11) Butyldiglycol | 3.67 | 3.67 |
| 12) Maincote HG-54[h] | 58.70 | 58.70 |
| 13) Texanol[i] | 1.50 | 1.50 |
| 14) Dibutyl phthalate[k] | 1.50 | 1.50 |
| 15) Sodium nitrite (13.8% in water)[l] | 0.80 | 0.80 |
| 16) Drew T 4310[m] | 0.32 | 0.32 |
| 17) Ammonia solution (25%) | 0.30 | 0.30 |
| Total | 100.00 | 100.00 |

For notes a) to m) see Table 2.

The application of the formulation to steel panels of type Q-Panel R, the implementation of the humidity test (330 hours) and the determination of the corrosion protection factors CPF are effected by analogy with the method described in Example 4. The results are compiled in Table 11. The larger the numbers, the better the protection against corrosion.

TABLE 11

| Coating composition | Humidity test, 330 hours | | |
|---|---|---|---|
| | CPF film | CPF metal | CPF |
| Example 8a | 4.8 | 3.0 | 7.8 |
| Example 8b | 6.0 | 6.0 | 12.0 |

EXAMPLE 9

Testing of BACO LV 9-bound 3-(4-methylbenzoyl)propionic acid (compound (106)) in acrylic dispersion based on Maincote HG-54, as corrosion inhibitor.

The coating composition based on Maincote HG-54 is prepared in analogy to Example 4, employing components 1 to 17 in the order given (cf. Table 12).

TABLE 12

Acrylic dispersion based on Maincote HG-54

| Composition | Example 9a % by weight | Example 9b % by weight |
|---|---|---|
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |
| 6) Acrysol RM 8[e] | 0.60 | 0.60 |
| 7) Bayferrox 130 ME[f] | 5.72 | 5.72 |
| 8) Millicarb[g] | 13.25 | 13.25 |
| 9) BACO LV 9 | 5.70 | — |
| 10) Corrosion inhibitor (compound (106)) | — | 5.70 |
| 11) Butyldiglycol | 3.67 | 3.67 |
| 12) Maincote HG-54[h] | 58.70 | 58.70 |
| 13) Texanol[i] | 1.50 | 1.50 |

TABLE 12-continued

Acrylic dispersion based on Maincote HG-54

| Composition | Example 9a % by weight | Example 9b % by weight |
|---|---|---|
| 14) Dibutyl phthalate[k] | 1.50 | 1.50 |
| 15) Sodium nitrite (13.8% in water)[l] | 0.80 | 0.80 |
| 16) Drew T 4310[m] | 0.32 | 0.32 |
| 17) Ammonia solution (25%) | 0.30 | 0.30 |
| Total | 100.00 | 100.00 |

For notes a) to m) see Table 2.

The application of the formulation to steel panels of type Q-Panel R, the implementation of the humidity test (330 hours) and the determination of the corrosion protection factors CPF are effected by analogy with the method described in Example 4. The results are compiled in Table 13. The larger the numbers, the better the protection against corrosion.

TABLE 13

| Coating composition | Humidity test, 330 hours | | |
|---|---|---|---|
| | CPF film | CPF metal | CPF |
| Example 9a | 4.5 | 5.0 | 9.5 |
| Example 9b | 5.6 | 6.0 | 11.6 |

EXAMPLE 10

Testing of BACO SF 7-bound 3-(4-methylbenzoyl)propionic acid (compound (107)) in acrylic dispersion based on Maincote HG-54, as corrosion inhibitor.

The coating composition based on Maincote HG-54 is prepared in analogy to Example 4, employing components 1 to 17 in the order given (cf. Table 14).

TABLE 14

Acrylic dispersion based on Maincote HG-54

| Composition | Example 10a % by weight | Example 10b % by weight |
|---|---|---|
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |
| 6) Acrysol RM 8[e] | 0.60 | 0.60 |
| 7) Bayferrox 130 ME[f] | 5.72 | 5.72 |
| 8) Millicarb[g] | 12.85 | 12.85 |
| 9) BACO SF 7 | 4.55 | — |
| 10) Corrosion inhibitor (compound (107)) | — | 4.55 |
| 11) Butyldiglycol | 3.67 | 3.67 |
| 12) Maincote HG-54[h] | 58.70 | 58.70 |
| 13) Texanol[i] | 1.50 | 1.50 |
| 14) Dibutyl phthalate[k] | 1.50 | 1.50 |
| 15) Sodium nitrite (13.8% in water)[l] | 0.80 | 0.80 |
| 16) Drew T 4310[m] | 0.32 | 0.32 |
| 17) Ammonia solution (25%) | 0.30 | 0.30 |
| Total | 100.00 | 100.00 |

For notes a) to m) see Table 2.

The application of the formulation to steel panels of type Q-Panel R, the implementation of the humidity test (330 hours) and the determination of the corrosion protection factors CPF are effected by analogy with the method described in Example 4. The results are compiled in Table 15. The larger the numbers, the better the protection against corrosion.

TABLE 15

| Coating composition | Humidity test, 330 hours | | |
|---|---|---|---|
| | CPF film | CPF metal | CPF |
| Example 10a | 4.0 | 3.0 | 7.0 |
| Example 10b | 5.6 | 6.0 | 11.6 |

EXAMPLE 11

Testing of Pergopak M3-bound 3-(4-methylbenzoyl)propionic acid (compound (108)) in acrylic dispersion based on Maincote HG-54, as corrosion inhibitor.

The coating composition based on Maincote HG-54 is prepared in analogy to Example 4, employing components 1 to 17 in the order given (cf. Table 16).

TABLE 16

Acrylic dispersion based on Maincote HG-54

| Composition | Example 11a % by weight | Example 11b % by weight |
|---|---|---|
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |
| 6) Acrysol RM 8[e] | 0.60 | 0.60 |
| 7) Bayferrox 130 ME[f] | 5.72 | 5.72 |
| 8) Millicarb[g] | 15.50 | 15.50 |
| 9) Pergopak M3 | 1.90 | — |
| 10) Corrosion inhibitor (compound (108)) | — | 1.90 |
| 11) Butyldiglycol | 3.67 | 3.67 |
| 12) Maincote HG-54[h] | 58.70 | 58.70 |
| 13) Texanol[i] | 1.50 | 1.50 |
| 14) Dibutyl phthalate[k] | 1.50 | 1.50 |
| 15) Sodium nitrite (13.8% in water)[l] | 0.80 | 0.80 |
| 16) Drew T 4310[m] | 0.32 | 0.32 |
| 17) Ammonia solution (25%) | 0.30 | 0.30 |
| Total | 100,00 | 100,00 |

For notes a) to m) see Table 2.

The application of the formulation to steel panels of type Q-Panel R, the implementation of the humidity test (330 hours) and the determination of the corrosion protection factors CPF are effected by analogy with the method described in Example 4. The results are compiled in Table 17. The larger the numbers, the better the protection against corrosion.

TABLE 17

| Coating composition | Humidity test, 330 hours | | |
|---|---|---|---|
| | CPF film | CPF metal | CPF |
| Example 11a | 3.0 | 1.3 | 4.3 |

TABLE 17-continued

| | Humidity test, 330 hours | | |
|---|---|---|---|
| Coating composition | CPF film | CPF metal | CPF |
| Example 11b | 5.5 | 6.0 | 11.5 |

EXAMPLE 12

Testing of ®BACO FR F 85-bound 3-(4-methylbenzoyl-)propionic acid (compound (111)) in acrylic dispersion based on Maincote HG-54, as corrosion inhibitor.

The coating composition based on Maincote HG-54 is prepared in analogy to Example 4, employing components 1 to 17 in the order given (cf. Table 18).

TABLE 18

Acrylic dispersion based on Maincote HG-54

| Composition | Example 12a % by weight | Example 12b % by weight |
|---|---|---|
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |
| 6) Acrysol RM 8[e] | 0.60 | 0.60 |
| 7) Bayferrox 130 ME[f] | 5.72 | 5.72 |
| 8) Millicarb[g] | 15.05 | 15.05 |
| 9) BACO FR F 85 | 2.35 | — |
| 10) Corrosion inhibitor (compound (111)) | — | 2.35 |
| 11) Butyldiglycol | 3.67 | 3.67 |
| 12) Maincote HG-54[h] | 58.70 | 58.70 |
| 13) Texanol[i] | 1.50 | 1.50 |
| 14) Dibutyl phthalate[k] | 1.50 | 1.50 |
| 15) Sodium nitrite (13.8% in water)[l] | 0.80 | 0.80 |
| 16) Drew T 4310[m] | 0.32 | 0.32 |
| 17) Ammonia solution (25%) | 0.30 | 0.30 |
| Total | 100.00 | 100.00 |

For notes a) to m) see Table 2.

The application of the formulation to steel panels of type Q-Panel R, the implementation of the salt spray test (168 hours) and the determination of the corrosion protection factors CPF are effected by analogy with the method described in Example 4. The results are compiled in Table 19. The larger the numbers, the better the protection against corrosion.

TABLE 19

| | Salt spray test, 168 hours | | |
|---|---|---|---|
| Coating composition | CPF film | CPF metal | CPF |
| Example 12a | 2.6 | 2.3 | 4.9 |
| Example 12b | 4.0 | 5.8 | 9.8 |

EXAMPLE 13

Testing of ®BACO FR F 85-bound 3-(4-chlorobenzoyl-)propionic acid (compound (113), Example 2) in acrylic dispersion based on Maincote HG-54, as corrosion inhibitor.

The coating composition based on Maincote HG-54 is prepared in analogy to Example 4, employing components 1 to 17 in the order given (cf. Table 20).

TABLE 20

Acrylic dispersion based on Maincote HG-54

| Composition | Example 13a % by weight | Example 13b % by weight |
|---|---|---|
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |
| 6) Acrysol RM 8[e] | 0.60 | 0.60 |
| 7) Bayferrox 130 ME[f] | 5.72 | 5.72 |
| 8) Millicarb[g] | 15.05 | 15.05 |
| 9) BACO FR F 85 | 2.35 | — |
| 10) Corrosion inhibitor (compound (113)) | — | 2.35 |
| 11) Butyldiglycol | 3.67 | 3.67 |
| 12) Maincote HG-54[h] | 58.70 | 58.70 |
| 13) Texanol[i] | 1.50 | 1.50 |
| 14) Dibutyl phthalate[k] | 1.50 | 1.50 |
| 15) Sodium nitrite (13.8% in water)[l] | 0.80 | 0.80 |
| 16) Drew T 4310[m] | 0.32 | 0.32 |
| 17) Ammonia solution (25%) | 0.30 | 0.30 |
| Total | 100.00 | 100.00 |

For notes a) to m) see Table 2.

The application of the formulation to steel panels of type Q-Panel R, the implementation of the humidity test (330 hours) and the determination of the corrosion protection factors CPF are effected by analogy with the method described in Example 4. The results are compiled in Table 21. The larger the numbers, the better the protection against corrosion.

TABLE 21

| | Humidity test, 330 hours | | |
|---|---|---|---|
| Coating composition | CPF film | CPF metal | CPF |
| Example 13a | 2.0 | 2.0 | 4.0 |
| Example 13b | 2.8 | 4.0 | 6.8 |

EXAMPLE 14

Testing of ®BACO FR F 85-bound 3-(4-methoxybenzoyl)propionic acid (compound (114), Example 3) in acrylic dispersion based on Maincote HG-54, as corrosion inhibitor.

The coating composition based on Maincote HG-54 is prepared in analogy to Example 4, employing components 1 to 17 in the order given (cf. Table 22).

TABLE 22

Acrylic dispersion based on Maincote HG-54

| Composition | Example 14a % by weight | Example 14b % by weight |
|---|---|---|
| 1) Deionized water | 3.10 | 3.10 |
| 2) Methylcarbitol[a] | 5.00 | 5.00 |
| 3) Orotan 165[b] | 0.82 | 0.82 |
| 4) Triton CF 10[c] | 0.29 | 0.29 |
| 5) Drew Plus TS 4380[d] | 0.28 | 0.28 |

TABLE 22-continued

Acrylic dispersion based on Maincote HG-54

| Composition | Example 14a % by weight | Example 14b % by weight |
|---|---|---|
| 6) Acrysol RM 8[e] | 0.60 | 0.60 |
| 7) Bayferrox 130 ME[f] | 5.72 | 5.72 |
| 8) Millicarb[g] | 15.05 | 15.05 |
| 9) BACO FR F 85 | 2.35 | — |
| 10) Corrosion inhibitor (compound (114)) | — | 2.35 |
| 11) Butyldiglycol | 3.67 | 3.67 |
| 12) Maincote HG-54[h] | 58,70 | 58,70 |
| 13) Texanol[j] | 1.50 | 1.50 |
| 14) Dibutyl phthalate[k] | 1.50 | 1.50 |
| 15) Sodium nitrite (13.8% in water)[l] | 0.80 | 0.80 |
| 16) Drew T 4310[m] | 0.32 | 0.32 |
| 17) Ammonia solution (25%) | 0.30 | 0.30 |
| Total | 100.00 | 100.00 |

For notes a) to m) see Table 2.

The application of the formulation to steel panels of type Q-Panel R, the implementation of the humidity test (330 hours) and the determination of the corrosion protection factors CPF are effected by analogy with the method described in Example 4. The results are compiled in Table 23. The larger the numbers, the better the protection against corrosion.

TABLE 23

| Coating composition | Humidity test, 330 hours | | |
|---|---|---|---|
| | CPF film | CPF metal | CPF |
| Example 14a | 2.0 | 2.0 | 4.0 |
| Example 14b | 2.0 | 4.6 | 6.6 |

EXAMPLE 15

Testing of ®BACO FR F 85-bound 3-(4-methylbenzoyl)propionic acid (compound (111)) in aqueous dispersion based on an acrylic ester/styrene copolymer (Acronal S 760), as corrosion inhibitor.

The coating composition based on Acronal S 760 is prepared first by premixing components 1 to 5, then adding components 6 and 7 (formulation without corrosion inhibitor) or 6 to 8 (formulation with corrosion inhibitor, compound (111), Example 1) in the order given (cf. Table 24).

TABLE 24

Aqueous dispersion based on Acronal S 760

| Composition | Example 15a % by weight | Example 15b % by weight |
|---|---|---|
| 1) Deionized water | 8.20 | 8.20 |
| 2) Pigment dispersant NL[a] | 0.15 | 0.15 |
| 3) Acronal S 760 (50% supply form)[b] | 8.00 | 8.00 |
| 4) Shellsol D 60[c] | 1.00 | 1.00 |
| 5) Agitan 280[d] | 0.30 | 0.30 |
| 6) Millicarb[e] | 18.00 | 15.15 |
| 7) Bayferrox 130 M[f] | 10.00 | 10.00 |
| 8) Corrosion inhibitor (compound (111)) | — | 2.85 |
| 9) Acronal S-760 (50% supply form)[b] | 49.00 | 49.00 |
| 10) Agitan 280[d] | 0.30 | 0.30 |

TABLE 24-continued

Aqueous dispersion based on Acronal S 760

| Composition | Example 15a % by weight | Example 15b % by weight |
|---|---|---|
| 11) Collacral PU 85/butyldiglycol[g] | 4.10 | 4.10 |
| 12) Deionized water | 0.95 | 0.95 |
| Total | 100.00 | 101.14 |

[a] ®Pigment dispersant NL: BASF AG; [b] ®Acronal S 760: acrylic ester/styrene copolymer (aqueous dispersion, BASF AG); [c] ®Shellsol D 60: petroleum spirit for coatings (Shell); [d] Agitan 280: antifoam (Münzing Chemie GmbH); [e] ®Millicarb: calcium carbonate (Firma Omya); [f] Bayferrox 130 M: red iron oxide (Bayer AG); [g] ®Collacral PU 85: thickener (BASF AG).

The resulting pigment paste is dispersed to a particle fineness <15 μm using a horizontal ball mill or the like. The particle fineness is assessed on the basis of the grindometer value (ISO 1524).

To complete the preparation of (make up) the coating material, components 9 to 12 are then added in the order given (Table 24). Application is effected by conventional spraying.

Depending on the desired viscosity, the finished coating material can be diluted by adding butyldiglycol/deionized water (1:1 g/g).

The coating material is applied to steel panels of the Bonder type in a coat thickness which, after drying, is 100 μm (drying conditions: 14 days at room temperature).

Before the commencement of weathering, the "coating films" are subjected to defined damage in the form of a parallel cut (i.e. parallel to the longest panel edge) using a Bonder crosshatch instrument (model 205; manufacturer/marketing: Lau, Hemer/Germany). The panel edges are protected by applying an edge protector (®Icosit 255; manufacturer: Inertol AG, Winterthur, Switzerland).

The samples are then subjected to rapid weathering by the salt-spray test (DIN 50 021 SS) for 168 hours. The corrosion protection factors (CPF) are determined by analogy with the method described in Example 4. The results are compiled in Table 25. The larger the numbers, the better the protection against corrosion.

TABLE 25

| Coating composition | Salt-spray test (DIN 50 021 SS), 168 hours | | |
|---|---|---|---|
| | CPF film | CPF metal | CPF |
| Example 15a | 2.4 | 2.6 | 5.0 |
| Example 15b | 3.4 | 6.0 | 9.4 |

EXAMPLE 16

Testing of ®BACO FR F 85-bound 3-(4-methylbenzoyl)propionic acid (compound (111)) in a water-thinnable 2-component epoxy resin formulation based on Beckopox EP 384 W/Beckopox EP 075/Beckopox EH 623 W, as corrosion inhibitor.

The coating composition based on Beckopox EP 384 W/Beckopox EP 075/Beckopox EH 623 W is prepared by employing components 1 to 8 (formulation without additives) or components 1 to 9 (formulation with additive) in the order given (component A, cf. Table 26).

TABLE 26

Water thinnable 2-component epoxy resin formulation based on Beckopox EP 384 W/Beckopox EP 075/ Beckopox EH 623 W

| Composition | Example 16a % by weight | Example 16b % by weight |
|---|---|---|
| Component A: | | |
| 1) Beckopox EH 623 W(80% supply form)[a] | 14.4 | 14.4 |
| 2) Deionized water | 29.2 | 29.2 |
| 3) Talc AT Extra[b] | 13.8 | 13.8 |
| 4) Bayferrox 130 M[c] | 12.0 | 12.0 |
| 5) Millicarb[d] | 27.3 | 22.2 |
| 6) Bentone SD 2[e] | 0.70 | 0.70 |
| 7) Borchigel L 75 (25% supply form)[f] | 1.70 | 1.70 |
| 8) Additol XL 270[g] | 0.9 | 0.9 |
| 9) Corrosion inhibitor (compound (111)) | — | 5.1 |
| Total | 100.00 | 103.10 |
| Component B: | | |
| 10) Beckopox EP 384 W(54% supply form)[h] | 63.0 | 63.0 |
| 11) Beckopox EP 075[i] | 3.7 | 3.7 |

[a] ®Beckopox EH 623 W: polyamine curing agent (Hoechst AG); [b] ®Talc AT Extra: Norwegian; [c] ®Bayferrox 130 M: red iron oxide (Bayer AG); [d] ®Millicarb: calcium carbonate (Omya); [e] ®Bentone SD 2: anti-settling agent (Kronos Titan GmbH); [f] ®Borchigel L 75: thickener/rheology improver (Gebr. Borchers AG); [g] ®Additol XL antifloating/dispersion auxiliary (Hoechst AG); [h] ®Beckopox EP 384 W: resin (Hoechst AG); [i] ®Beckopox EP 075: reactive diluent (polypropylene glycol diglycidyl ether (Hoechst AG)).

The resulting component A (formulation with and without corrosion inhibitor) is dispersed to a particle fineness <15 μm using a horizontal ball mill. The result of dispersion is assessed by determining the grindometer value (ISO 1524).

For application, 100 g of component A are mixed with 66.7 g of component B. To adjust to the desired spray viscosity, the coating material is diluted with demineralized water. The material is applied to steel panels (19×10.5 cm) of Bonder type (cold-rolled, degreased steel; manufacturer: Chemetall, Frankfurt am Main/Germany) in a coat thickness which, after drying, is 60 μm (drying conditions: 10 days at room temperature).

Before the commencement of weathering, the "coating films" are subjected to defined damage in the form of a parallel cut (i.e. parallel to the longest panel edge) using a Bonder crosshatch instrument (model 205; manufacturer/ marketing: Lau, Hemer/Germany). The panel edges are protected by applying an edge protector (®Icosit 255; manufacturer: Inertol AG, Winterthur, Switzerland).

The samples are then subjected to rapid weathering by the salt-spray test (DIN 50 021 SS) for 168 hours. The corrosion protection factors CPF are determined by analogy with the method described in Example 4. The results are compiled in Table 27. The larger the numbers, the better the protection against corrosion.

TABLE 27

Salt-spray test (DIN 50 021 SS), 168 hours

| Coating composition | CPF film | CPF metal | CPF |
|---|---|---|---|
| Example 16a | 2.0 | 1.3 | 3.3 |
| Example 16b | 4.2 | 4.0 | 8.2 |

EXAMPLE 17

Testing of ®BACO FR F 85-bound 3-(4-methylbenzoyl) propionic acid (compound (111)) in a water-thinnable alkyd/ urethane formulation based on Resydrol AZ 436 W/Daotan VTW 1237, as corrosion inhibitor.

The coating composition based on Resydrol AZ 436 W/Daotan VTW 1237 is prepared by employing components 1 to 12 in the order given (cf. Table 28).

TABLE 28

Water-thinnable alkyd/urethane formulation based on Resydrol AZ 436 W/Daotan VTW 1237

| Composition | Example 17a % by weight | Example 17b % by weight |
|---|---|---|
| 1) Resydrol AZ 436 W[a] | 28.3 | 28.3 |
| 2) Ammonia solution (10%) | 0.1 | 0.1 |
| 3) Additol VXW 4940 (1:1 in water)[b] | 0.6 | 0.6 |
| 4) Daotan VTW 1237 (32% supply form)[c] | 39.8 | 39.8 |
| 5) Surfynol SE[d] | 0.3 | 0.3 |
| 6) Additol VXW 4973[e] | 0.3 | 0.3 |
| 7) Borchigel L 75 (25% supply form)[f] | 2.0 | 2.0 |
| 8) Talc AT Extra[g] | 7.3 | 7.3 |
| 9) Bayferrox 130 M[h] | 6.4 | 6.4 |
| 10) Millicarb[i] | 11.8 | 9.25 |
| 11) Corrosion inhibitor (compound (111)) | — | 2.55 |
| 12) Deionized water | 3.1 | 3.1 |
| Total | 100.00 | 100.00 |

[a] ®Resydrol AZ 436 W: alkyd resin emulsion (Hoechst AG); [b] ®Additol VXW 4940: drying substance (metal drier based on Co, Zr, Ba)(Hoechst AG); [c] ®Daotan VTW 1237: polyurethane emulsion (Hoechst AG); [d] ®Surfynol SE: nonionic wetting agent (Air Products and Chemicals); [e] ®Additol VXW 4973: antifoam (Hoechst AG); [f] ®Borchigel L 75: thickener (Gebrüder Botchers AG); [g] ®Talc AT Extra: "Norwegian Talc"; [h] ®Bayferrox 130 M: red iron oxide (Bayer AG); [i] ®Millicarb: calcium carbonate (Firma Omya).

The coating composition based on Resydrol AZ 436 W/Daotan VTW 1237 is prepared by first adjusting Resydrol AZ 436 W (component 1) to a pH of 8.5 using ammonia solution (component 2). Component 3 is then incorporated thoroughly by dispersion. Daotan VTW 1237 (component 4) is then stirred into components 1 to 3, the pH is checked and is adjusted, if required, to pH=8.5 with ammonia solution. Then components 5 to 12 are added in the order given, with the coating material batch being only partly dispersed (so-called partial dissolvers). After it has been left to stand overnight the batch is dispersed to a particle fineness of <15 μm. The degree of particle fineness obtained is assessed on the basis of the grindometer value (ISO 1524). For conventional spraying the coating material is adjusted to the desired spray viscosity using deionized water.

The coating material is applied to steel panels (19×10.5 cm) of the Bonder type (cold-rolled, degreased steel; manufacturer: Chemetall, Frankfurt am Main/Germany) in a coat thickness which, after drying, is 50 μm (drying conditions: 14 days at room temperature).

Before the commencement of weathering, the "coating films" are subjected to defined damage in the form of a parallel cut (i.e. parallel to the longest panel edge) using a Bonder crosshatch instrument (model 205; manufacturer/marketing: Lau, Hemer/Germany). The panel edges are protected by applying an edge protector (®Icosit 255; manufacturer: Inertol AG, Winterthur, Switzerland).

The samples are then subjected to rapid weathering by the salt-spray test (DIN 50 021 SS) for 120 hours. The corrosion protection factors CPF are determined by analogy with the method described in Example 4. The results are compiled in Table 29. The larger the numbers, the better the protection against corrosion.

TABLE 29

Salt-spray test (DIN 50 021 SS), 120 hours

| Coating composition | CPF film | CPF metal | CPF |
|---|---|---|---|
| Example 17a | 2.0 | 2.5 | 4.5 |
| Example 17b | 4.2 | 4.2 | 7.6 |

What is claimed is:

1. A carrier-bound compound of the formula I

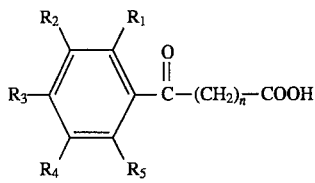

in which $R_1, R_2, R_3, R_4$ and $R_5$ independently of one another are hydrogen, halogen, nitro, cyano, $CF_3$, $C_1$–$C_{15}$alkyl, $C_5$–$C_{12}$cycloalkyl, $C_2$–$C_{15}$alkenyl, $C_1$–$C_{12}$haloalkyl, $C_1$–$C_{12}$alkoxy, $C_1$–$C_{12}$alkylthio, $C_6$–$C_{10}$aryl, $C_6$–$C_{10}$aryloxy, $C_7$–$C_{12}$arylalkyl, —$CO_2R_6$, —$COR_6$ or

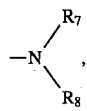

in which at least one of the radicals $R_1$ to $R_5$ is hydrogen, halogen or $C_1$–$C_{15}$alkyl, or, alternatively, the radicals $R_1$ and $R_2$, $R_2$ and $R_3$, $R_3$ and $R_4$ or $R_4$ and $R_5$ together with the carbon atoms to which they are attached form a benzo or cyclohexenyl ring, $R_6$ is $C_1$–$C_{20}$alkyl, $C_2$–$C_{20}$alkyl which is interrupted by oxygen, sulfur or >N—$R_9$; or is $C_7$–$C_{12}$arylalkyl, $R_7$ and $R_8$ independently of one another are hydrogen, $C_1$–$C_{24}$alkyl or $C_2$–$C_{24}$alkyl which is interrupted by oxygen, sulfur or >N—$R_9$, $R_9$ is hydrogen or $C_1$–$C_8$alkyl, and n is an integer from the range from 1 to 10.

2. A carrier-bound compound according to claim 1, in which at least two of the radicals $R_1$ to $R_5$ are hydrogen.

3. A carrier-bound compound according to claim 1, in which $R_1$ is hydrogen, $R_2, R_3, R_4$ and $R_5$ independently of one another are hydrogen, chlorine, bromine, nitro, cyano, $CF_3$, $C_1$–$C_8$alkyl, $C_5$–$C_7$cycloalkyl, $C_2$–$C_8$alkenyl, $C_1$–$C_8$alkoxy, $C_1$–$C_8$alkylthio, phenyl, phenyloxy, benzyl, —$CO_2R_6$, —$COR_6$ or

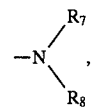

$R_6$ is $C_1$–$C_{12}$alkyl, $C_2$–$C_{12}$alkyl which is interrupted by oxygen; or is benzyl, $R_7$ and $R_8$ independently of one another are hydrogen, $C_1$–$C_8$alkyl or $C_2$–$C_{12}$alkyl which is interrupted by oxygen, and n is an integer from the range from 1 to 5.

4. A carrier-bound compound according to claim 1, in which $R_1, R_2$ and $R_4$ are hydrogen, $R_3$ and $R_5$ independently of one another are hydrogen, chlorine, bromine, $CF_3$, $C_1$–$C_8$alkyl, cyclohexyl, $C_1$–$C_8$alkoxy, —$CO_2R_6$, —$COR_6$ or

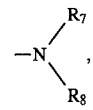

$R_6$ is $C_1$–$C_8$alkyl, $R_7$ and $R_8$ independently of one another are hydrogen or $C_1$–$C_8$alkyl, and n is an integer in the range from 2 to 4.

5. A carrier-bound compound according to claim 1, in which $R_1, R_2, R_4$ and $R_5$ are hydrogen and n is 2.

6. A carrier-bound compound according to claim 1, in which $R_1, R_2, R_4$ and $R_5$ are hydrogen, $R_3$ is hydrogen, $C_1$–$C_4$alkyl, $C_1$–$C_4$alkoxy or chlorine, and n is 2.

7. A carrier-bound compound according to claim 1, in which the carrier is a filler or a pigment.

8. A carrier-bound compound according to claim 1, in which the carrier is a filler based on oxide, hydroxide, silicate or carbonate.

9. A carrier-bound compound according to claim 1, in which the carrier is alumina, magnesium oxide, aluminium hydroxide, magnesium hydroxide, kieselguhr, talc, aluminium silicate, calcium carbonate, iron oxide or a urea/formaldehyde adduct.

10. A carrier-bound compound according to claim 1, in which the carrier is aluminium hydroxide.

11. A carrier-bound compound according to claim 1, in which the compounds of the formula I are present, with respect to the total weight, in a proportion of from 5 to 70% by weight.

12. A coating composition comprising a) an organic film forming binder and b) an effective corrosion inhibiting amount of at least one carrier-bound compound of the formula I

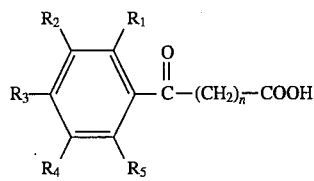

in which $R_1, R_2, R_3, R_4$ and $R_5$ independently of one another are hydrogen, halogen, nitro, cyano, $CF_3$, $C_1$–$C_{15}$ alkyl, $C_5$–$C_{12}$ cycloalkyl, $C_2$–$C_{15}$ alkenyl, $C_1$–$C_{12}$ haloalkyl, $C_1$–$C_{12}$ alkoxy, $C_1$–$C_{12}$ alkylthio, $C_6$–$C_{10}$ aryl, $C_6$–$C_{10}$ aryloxy $C_7$–$C_{12}$ arylalkyl, —$CO_2R_6$, —$COR_6$ or

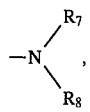

in which at least one of the radicals $R_1$ to $R_5$ is hydrogen, halogen, or $C_1$–$C_{15}$ alkyl, or, alternatively, the radicals $R_1$ and $R_2$, $R_2$ and $R_3$, $R_3$ and $R_4$, or $R_4$ and $R_5$ together with the carbon radicals to which they are attached form a benzo or cyclohexenyl ring, $R_6$ is $C_1$–$C_{20}$ alkyl, $C_2$–$C_{20}$ alkyl which is interrupted by oxygen, sulfur or >N—$R_9$; or is $C_7$–$C_{12}$ arylalkyl, $R_7$ and $R_8$ independently of one another are $C_1$–$C_{24}$ alkyl or $C_2$–$C_{24}$ alkyl which is interrupted by oxygen, sulfur or >N—$R_9$, $R_9$ is hydrogen or $C_1$–$C_8$ alkyl, and n is an integer from the range from 1 to 10.

13. A coating composition according to claim 12, in which the coating composition is a paint system.

14. A coating composition according to claim 12, in which the coating composition is an aqueous paint system.

15. A coating composition according to claim 12, in which component a) is an epoxy resin, a polyurethane resin, a polyester resin, an acrylic resin, an acrylic copolymer resin, a polyvinyl resin, a phenolic resin, an alkyd resin, or a mixture of said resins.

16. A coating composition according to claim 12, additionally comprising one or more components selected from pigments, dyes, fillers, flow control agents, dispersants, thixotropic agents, adhesion promoters, antioxidants, light stabilizers or curing catalysts.

17. A coating composition according to claim 12, in which component b) is present in a proportion of from 0.1 to 20% based on the total solids content of the coating composition.

18. A method of protecting a corrodable metallic substrate, which comprises applying to said substrate a coating composition according to claim 12 and then drying and optionally curing said composition.

* * * * *